United States Patent
Rangavajla et al.

(10) Patent No.: US 10,251,899 B2
(45) Date of Patent: Apr. 9, 2019

(54) METHOD FOR IMPROVING STOOL CHARACTERISTICS IN INFANTS

(75) Inventors: Nagendra Rangavajla, Newburgh, IN (US); Joaquin Franco, Newburgh, IN (US)

(73) Assignee: MEAD JOHNSON NUTRITION COMPANY, Evansville, IN (US)

( * ) Notice: Subject to any disclaimer, the term of this patent is extended or adjusted under 35 U.S.C. 154(b) by 1502 days.

(21) Appl. No.: 12/102,077

(22) Filed: Apr. 14, 2008

(65) Prior Publication Data

US 2009/0092590 A1    Apr. 9, 2009

Related U.S. Application Data

(60) Provisional application No. 60/978,172, filed on Oct. 8, 2007.

(51) Int. Cl.
*A61K 31/702* (2006.01)
*A61K 31/7016* (2006.01)
*A61K 35/745* (2015.01)
*A61K 35/747* (2015.01)

(52) U.S. Cl.
CPC ........ *A61K 31/702* (2013.01); *A61K 31/7016* (2013.01); *A61K 35/745* (2013.01); *A61K 35/747* (2013.01)

(58) Field of Classification Search
None
See application file for complete search history.

(56) References Cited

U.S. PATENT DOCUMENTS

| | | | |
|---|---|---|---|
| 5,472,952 A | 12/1995 | Smidt et al. | |
| 6,358,580 B1 * | 3/2002 | Mang et al. | 428/35.7 |
| 7,101,565 B2 | 9/2006 | Monte | |
| 7,205,145 B2 * | 4/2007 | Ryan | 435/309.1 |
| 7,572,474 B2 * | 8/2009 | Petschow | A61K 31/721 424/439 |
| 7,576,070 B2 * | 8/2009 | Kunz et al. | 514/54 |
| 2004/0086491 A2 | 5/2004 | Monte | |
| 2004/0185032 A1 | 9/2004 | Burrell | |
| 2004/0248768 A1 | 12/2004 | Garcia-Rodenas et al. | |
| 2006/0165670 A1 | 7/2006 | Beer et al. | |

FOREIGN PATENT DOCUMENTS

| | | | |
|---|---|---|---|
| WO | WO 2006/019300 | * | 2/2006 |
| WO | WO 2006/112714 | * | 10/2006 |

OTHER PUBLICATIONS

Fanaro et al. "Acidic oligosaccharide from pectin hydrolysate as new component for infant formulae: effect on intestinal flora, stool characteristic and pH". Journal of Pediatric Gastroenterology and Nutrition. Aug. 2005, vol. 41, No. 2, pp. 186-190.*
Kunz, et al., *Oligosaccharides in Human Milk: Structure, Functional, and Metabolic Aspects*, Ann. Rev. Nutr. 20:699-722 (2000).
Newburg, *Do the Binding Properties of Oligosaccharides in Milk Protect Human Infants from Gastrointestinal Bacteria?*, J. Nutr. 217:S980-s984 (1997).
Rivero-Urgell, et al., *Oligosaccharides: Application in Infant Food*, Early Hum. Dev. 65(S):43-52 (2001).
Gibson, G.R., et al., *Dietary Modulation of the Human Colonic Microbiota-Introducing the Concept of Probiotics*, J. Nutr. 125:1401-1412 (1995).
Lee, S. et al., *Determination of Total, Soluble and Insoluble Dietary Fiber in Foods—enzymatic-gravimetric Method, Mes-Tris Buffer: Collaborative Study*, J.A.O.A.C Int. 75:395-416 (1992).
Titgemeyer, E.C., et al., *Fermentability of Various Fiber Sources by Human Fecal Bacteria in vitro*, American Journal of clinical Nutrition, 53:1418-1424 (1991).
Hillman, L., et al., *Differing effects of pectin, cellulose and lignin on stool pH, transit time and weight*, British Journal of Nutr. (1983), 50, 189-195.
21 CFR 172.841 (polydextrose), 1 page, dated Oct. 24, 2016.
21 CFR 184.1277 (dextrin), 1 page, dated Oct. 24, 2016.

* cited by examiner

*Primary Examiner* — Vera Afremova
(74) *Attorney, Agent, or Firm* — Troutman Sanders LLP; Ryan Schneider; Chris Davis

(57) ABSTRACT

In accordance with the present invention, a novel method for improving the stool characteristics, reducing the incidence of diarrhea, and firming the stool of a formula-fed infant has been discovered. The method comprises administering to the infant at least one prebiotic and hydrolyzed pectin.

15 Claims, No Drawings

METHOD FOR IMPROVING STOOL CHARACTERISTICS IN INFANTS

BACKGROUND OF THE INVENTION (1) Field of the Invention

The present invention relates to a method for improving stool characteristics in infants.

(2) Description of the Related Art

The infant gut microflora is rapidly established in the first few weeks following birth. The nature of this intestinal colonization is initially determined by early exposure to environmental sources of microbes as well as the health of the infant. Whether the infant is breast-fed or formula fed also has a strong influence on the intestinal bacterial population.

In the breast-fed infant, for example, *Bifidobacterium* spp. dominate among intestinal bacteria, with *Streptococcus* spp. and *Lactobacillus* spp. as less common contributors. In contrast, the microflora of formula-fed infants is more diverse, containing *Bifidobacterium* spp. and *Bacteroides* spp. as well as the more pathogenic species, *Staphylococcus*, *Escherichia coli* and *Clostridia*. The varied species of *Bifidobacterium* in the stools of breast-fed and formula-fed infants differ as well.

Bifidobacteria are generally considered "beneficial" bacteria and are known to protect against colonization by pathogenic bacteria. This likely occurs through competition for cell surface receptors, competition for essential nutrients, production of anti-microbial agents, and production of inhibitory compounds such as short chain fatty acids (SCFA) which may decrease fecal pH and inhibit potentially pathogenic bacteria. Bifidobacteria are also associated with resistance to gastrointestinal (GI) tract and respiratory infection as well as an enhanced immune function in children and infants. Therefore, the promotion of an intestinal environment in which Bifidobacteria dominate has become a goal in the development of nutritional formulations for formula-fed infants.

Human milk (HM) contains a number of factors that may contribute to the growth and population of Bifidobacteria in the gut microflora of infants. Among these factors is a complex mixture of more than 130 different oligosaccharides that reach levels as high as 8-12 g/L in transitional and mature milk. Kunz, et al., *Oligosaccharides in Human Milk: Structure, Functional and Metabolic Aspects,* Ann. Rev. Nutr. 20: 699-722 (2000). These oligosaccharides are resistant to enzymatic digestion in the upper gastrointestinal tract and reach the colon intact, where they serve as substrates for colonic fermentation.

HM oligosaccharides are believed to elicit an increase in the number of Bifidobacteria in the colonic flora, along with a reduction in the number of potentially pathogenic bacteria. Kunz, et al., *Oligosaccharides in Human Milk: Structure, Functional and Metabolic Aspects,* Ann. Rev. Nutr. 20: 699-722 (2000); Newburg, *Do the Binding Properties of Oligosaccharides in Milk Protect Human Infants from Gastrointestinal Bacteria?,* J. Nutr. 217:S980-S984 (1997). One way that HM oligosaccharides may increase the number of Bifidobacteria and reduce the number of potentially pathogenic bacteria is by acting as competitive receptors and inhibiting the binding of pathogens to the cell surface. Rivero-Urgell, et al., *Oligosaccharides: Application in Infant Food,* Early Hum. Dev. 65(S):43-52 (2001).

Because cow's milk and commercially available infant formulas that are based on cow's milk provide only trace amounts of oligosaccharides, however, prebiotics are often used to supplement the diet of formula-fed infants. Prebiotics have been defined as "non-digestible food ingredients that beneficially affect the host by selectively stimulating the growth and/or activity of one or a limited number of bacteria in the colon that can improve the health of the host". Gibson, G. R. & Roberfroid, M. B., *Dietary Modulation of the Human Colonic Microbiota-Introducing the Concept of Probiotics,* J. Nutr. 125:1401-1412 (1995). Common prebiotics include fructo-oligosaccharide, gluco-oligosaccharide, galacto-oligosaccharide, isomalto-oligosaccharide, xylo-oligosaccharide and lactulose.

Unfortunately, however, there are some disadvantages in the administration of prebiotics to formula-fed infants. While they may beneficially affect the population of beneficial bacteria in the gut, the fermentation of many of these prebiotic substances occurs at a very rapid rate, which often produces excess gas, abdominal distension, bloating, and diarrhea. Human milk contains very high levels of oligosaccharides, in fact, approximately 10% of the total carbohydrates are oligosaccharides. Adding such significant concentrations of prebiotics to infant formulas causes unusually loose stools and diarrhea. Diarrhea and loose stools can severely compromise infant health due to depletion of fluids, electrolytes, and other nutrients. Accordingly, it would be beneficial to provide prebiotics to an infant in a method that would benefit the gut microflora without producing unwanted side effects such as those discussed above.

SUMMARY OF THE INVENTION

Briefly, therefore, the present invention is directed to a novel method for improving the stool characteristics of a formula-fed infant, the method comprising administering to the infant at least one prebiotic and hydrolyzed pectin.

The invention is also directed to a novel method for producing firm stool in a formula-fed infant, the method comprising administering to the infant at least one prebiotic and hydrolyzed pectin.

In addition, the invention is directed to a novel method for reducing the incidence of diarrhea in a formula-fed infant, the method comprising administering to the infant at least one prebiotic and hydrolyzed pectin.

DETAILED DESCRIPTION OF THE PREFERRED EMBODIMENTS

Reference now will be made in detail to the embodiments of the invention, one or more examples of which are set forth below. Each example is provided by way of explanation of the invention, not a limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment.

Thus, it is intended that the present invention covers such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

As used herein, the term "prebiotic" means a non-digestible food ingredient that beneficially affects the host by selectively stimulating the growth and/or activity of one or a limited number of bacteria in the colon that can improve the health of the host.

The term "probiotic" means a microorganism with low or no pathogenicity that exerts beneficial effects on the health of the host.

As used herein, the term "infant" means a human that is less than about one year old.

As used herein, the term "infant formula" means a composition that satisfies the nutrient requirements of an infant by being a substitute for human milk. In the United States, the content of an infant formula is dictated by the federal regulations set forth at 21 C.F.R. Sections 100, 106, and 107. These regulations define macronutrient, vitamin, mineral, and other ingredient levels in an effort to stimulate the nutritional and other properties of human breast milk.

In accordance with the present invention, a novel method for improving the stool characteristics, reducing the incidence of diarrhea, and firming the stool of a formula-fed infant of a formula-fed infant has been discovered. The method comprises administering to the infant at least one prebiotic and hydrolyzed pectin.

The prebiotic used in the present invention can be any prebiotic known in the art. Examples of prebiotics useful herein include, but are not limited to: fructo-oligosaccharide, inulin, gluco-oligosaccharide, galacto-oligosaccharide, isomalto-oligosaccharide, xylo-oligosaccharide, soybean oligosaccharides, chito-oligosaccharide, gentio-oligosaccharide, manno-oligosacchaide, lactulose, lactosucrose, raffinose, aribino-oligosaccharide, glucans, siallyl-oligosaccharide, polydextrose, inulin, and fuco-oligosaccharide.

An effective amount of the prebiotic may be between about 1.0 g/L and 10.0 g/L, administered daily. In another embodiment, an effective amount of the prebiotic may be between about 2.0 g/L and 8.0 g/L, administered daily.

The invention relates to a method for improving stool characteristics via the administration of a prebiotic and hydrolyzed pectin. Pectin is a heterogeneous grouping of acidic structural polysaccharides, found in fruit and vegetables. Pectin consists mainly of galacturonic acid and galacturonic acid methyl ester units forming linear polysaccharide chains. It is normally classified according to its degree of esterification. Pectins are mainly used as gelling agents, but can also act as thickeners, water binders and stabilizers.

In the present invention, the pectin is hydrolyzed. The pectin may be partially or extensively hydrolyzed. The partially hydrolyzed pectin of the present invention has a peak molecular weight of less than unmodified or intact pectin and greater than 3,300. The extensively hydrolyzed pectin of the present invention has a peak molecular weight of 3,300 or less.

In an embodiment, the pectins for use herein have a peak molecular weight of 8,000 or greater. In other embodiments, the pectins of the invention have a peak molecular weight of between about 8,000 and about 500,000. In still other embodiments, the pectins of the invention have a peak molecular weight of between about 10,000 and about 200,000. In a particular embodiment, the pectins of the invention have a peak molecular weight between about 15,000 and about 100,000.

The amount of hydrolyzed pectin present in the composition of the invention may be between about 0.1 g and about 5 g per 100 kcal of total composition. In another embodiment, the amount of hydrolyzed pectin present in the composition of the invention may be about 0.2 g to about 3 g per 100 kcal of total composition. In yet another embodiment, the amount of hydrolyzed pectin present in the composition of the invention may be about 0.25 g to about 1 g per 100 kcal of total composition.

The partially hydrolyzed pectins of the present invention can be prepared by any means known in the art to reduce molecular weight. Examples of said means are chemical hydrolysis, enzymatic hydrolysis and mechanical shear. A preferred means of reducing the molecular weight is by alkaline or neutral hydrolysis at elevated temperature, for example, 80° to 95° C.

In some embodiments of the invention, the method involves the administration of at least one prebiotic, a partially hydrolyzed pectin, and one or more insoluble fibers. The term "insoluble fiber" as used herein refers to a dietary fiber in which at least 60 weight % of the total dietary fiber is insoluble dietary fiber as determined by Lee, S. et al., "Determination of Total, Soluble and Insoluble Dietary Fiber in Foods-enzymatic-gravimetric Method, MES-TRIS Buffer: Collaborative Study", J.A.O.A.C Int. 75:395-416 (1992). Examples of insoluble fibers useful herein are oat hull fiber, soy fiber, pea fiber, beet fiber, cellulose and corn fiber. In a particular embodiment, the insoluble fibers for use herein are selected from the group consisting of soy fiber, oat hull fiber, and a mixture thereof. In this embodiment, the fiber system may comprise about 0.5 to about 20 weight % of partially hydrolyzed pectin. In another embodiment, the fiber system may comprise about 1 to about 10 weight % of partially hydrolyzed pectin.

For some applications it is desirable to use a combination of partially hydrolyzed pectin with one or more non-fermentable fibers. The term "non-fermentable" as used herein refers to a dietary fiber which has a fermentability of less than 40% as determined by the method described in U.S. Pat. No. 5,085,883, incorporated herein by reference, which is the same method described in Titgemeyer, et al, "Fermentability of Various Fiber Sources by Human Fecal Bacteria in vitro," American Journal of Clinical Nutrition, 53:1418-1424 (1991). Examples of non-fermentable fibers include carboxymethyl-cellulose, oat hull fiber, corn bran, mixtures thereof, and the like. Thus, a particular fiber system of the invention may comprise about 25 to 75 weight % of partially hydrolyzed pectin and about 25 to about 75 weight % of non-fermentable fiber. Another fiber system of the invention may comprise about 45 to about 55 weight % partially hydrolyzed pectin and about 45 to 55 weight % of non-fermentable fiber.

In an embodiment, the prebiotic and hydrolyzed pectin can be provided in a form suitable for infants selected from the group consisting of infant formula, follow-on formula, beverage, milk, yogurt, fruit juice, fruit-based drink, chewable tablet, cookie, cracker, or a combination thereof. In a particular embodiment, the prebiotic and hydrolyzed pectin of the invention may be administered to the infant via an infant formula. In this embodiment, the infant formula may be nutritionally complete and contain suitable types and amounts of lipid, carbohydrate, protein, vitamins and minerals. The amount of lipid or fat typically can vary from about 3 to about 7 g/100 kcal. The amount of protein typically can vary from about 1 to about 5 g/100 kcal. The amount of carbohydrate typically can vary from about 8 to about 12 g/100 kcal. Protein sources can be any used in the art, e.g., nonfat milk, whey protein, casein, soy protein, hydrolyzed protein, amino acids, and the like. Carbohydrate sources can be any used in the art, e.g., lactose, glucose, corn syrup solids, maltodextrins, sucrose, starch, rice syrup solids, and the like. Lipid sources can be any used in the art, e.g., vegetable oils such as palm oil, canola oil, corn oil, soybean oil, palmolein, coconut oil, medium chain triglyceride oil, high oleic sunflower oil, high oleic safflower oil, and the like.

Conveniently, commercially available nutritional compositions, infant formulas, human milk supplements, or children's nutritional products can be used. For example, Enfamil®, Enfamil® Premature Formula, Enfamil® with Iron, Enfamil® Gentlease® LIPIL®, Enfamil® LIPIL®, Lactofree®, Enfamil® Enfagrow®, Sustagen®, Nutramigen®, Pregestimil®, and ProSobee® (available from Mead Johnson & Company, Evansville, Ind., U.S.A.) may be supplemented with suitable levels of prebiotic and hydrolyzed pectin and used in practice of the method of the invention.

In some embodiments of the invention, long chain polyunsaturated fatty acids (LCPUFAs) may be administered in combination with the prebiotic and hydrolyzed pectin. The LCPUFAs may be administered separately from the prebiotic and hydrolyzed pectin or may be included as part of a nutritional composition, infant formula, human milk supplement, or children's nutritional product that contains a prebiotic and hydrolyzed pectin. In this embodiment, the LCPUFAs may include docosahexaenoic acid (DHA), arachidonic acid (ARA), and/or eicosapentaenoic acid (EPA).

If administered as part of the present invention, the weight ratio of ARA:DHA may be from about 1:3 to about 9:1. In one embodiment of the present invention, this ratio is from about 1:2 to about 4:1. In yet another embodiment, the ratio is from about 2:3 to about 2:1. In one particular embodiment the ratio is about 2:1. In another particular embodiment of the invention, the ratio is about 1:1.5. In other embodiments, the ratio is about 1:1.3. In still other embodiments, the ratio is about 1:1.9. In a particular embodiment, the ratio is about 1.5:1. In a further embodiment, the ratio is about 1.47:1.

If administered as part of the present invention, the level of DHA may be between about 0.0% and 1.00% of fatty acids, by weight. In other embodiments, the level of DHA may be about 0.32% by weight. In some embodiments, the level of DHA may be about 0.33% by weight. In another embodiment, the level of DHA may be about 0.64% by weight. In another embodiment, the level of DHA may be about 0.67% by weight. In yet another embodiment, the level of DHA may be about 0.96% by weight. In a further embodiment, the level of DHA may be about 1.00% by weight.

If administered as part of the present invention, the level of ARA may be between 0.0% and 0.67% of fatty acids, by weight. In another embodiment, the level of ARA may be about 0.67% by weight. In another embodiment, the level of ARA may be about 0.5% by weight. In yet another embodiment, the level of DHA may be between about 0.47% and 0.48% by weight.

If administered as part of the present invention, the amount of DHA may be from about 2 mg/100 kilocalories (kcal) to about 100 mg/100 kcal. In another embodiment, the amount of DHA may be from about 5 mg/100 kcal to about 75 mg/100 kcal. In yet another embodiment, the amount of DHA may be from about 15 mg/100 kcal to about 60 mg/100 kcal.

If administered as part of the present invention, the amount of ARA may be from about 4 mg/100 kilocalories (kcal) to about 100 mg/100 kcal. In another embodiment, the amount of ARA may be from about 10 mg/100 kcal to about 67 mg/100 kcal. In yet another embodiment, the amount of ARA may be from about 20 mg/100 kcal to about 50 mg/100 kcal. In a particular embodiment, the amount of ARA may be from about 25 mg/100 kcal to about 40 mg/100 kcal. In one embodiment, the amount of ARA is about 30 mg/100 kcal.

If administered as part of the present invention, the effective amount of DHA may be from about 3 mg per kg of body weight per day to about 150 mg per kg of body weight per day. In one embodiment of the invention, the amount is from about 6 mg per kg of body weight per day to about 100 mg per kg of body weight per day. In another embodiment the amount is from about 15 mg per kg of body weight per day to about 60 mg per kg of body weight per day.

If administered as part of the present invention, the effective amount of ARA may be from about 5 mg per kg of body weight per day to about 150 mg per kg of body weight per day. In one embodiment of this invention, the amount varies from about 10 mg per kg of body weight per day to about 120 mg per kg of body weight per day. In another embodiment, the amount varies from about 15 mg per kg of body weight per day to about 90 mg per kg of body weight per day. In yet another embodiment, the amount varies from about 20 mg per kg of body weight per day to about 60 mg per kg of body weight per day.

If the composition of the invention is supplemented with oils containing LCPUFAs, it may be accomplished using standard techniques known in the art. For example, an equivalent amount of an oil which is normally present in a composition, such as high oleic sunflower oil, may be replaced with the LCPUFAs.

If utilized, the source of the LCPUFAs can be any source known in the art such as marine oil, fish oil, single cell oil, egg yolk lipid, brain lipid, and the like. The LCPUFAs can be in natural form or refined form.

As an alternative to an infant formula administration, the prebiotic and hydrolyzed pectin of the present invention can be administered as a supplement not integral to the formula feeding. For example, the prebiotic and hydrolyzed pectin can be ingested in the form of a pill, tablet, capsule, caplet, powder, liquid or gel. In this embodiment, the prebiotic and hydrolyzed pectin can be ingested in combination with other nutrient supplements, such as vitamins, or in combination with a LCPUFA supplement, such as DHA or ARA.

In a particular embodiment of the invention, the method of the invention may involve the administration of at least one prebiotic, hydrolyzed pectin, and one or more probiotics to an infant. Any probiotic known in the art will be acceptable in this embodiment. In a particular embodiment, the probiotic is chosen from the group consisting of *Bifidobacterium* spp. or *Lactobacillus* spp. In an embodiment, the probiotic is *Lactobacillus rhamnosus* GG (LGG). In another embodiment, the probiotic is *Bifidobacterium lactis*.

All references cited in this specification, including without limitation, all papers, publications, patents, patent applications, presentations, texts, reports, manuscripts brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims. Therefore, the spirit and scope of the appended claims should not be limited to the description of the preferred versions contained therein.

What is claimed is:

1. A method for providing prebiotics to a formula-fed infant while producing firm stool in the infant, the method comprising administering to the infant a nutritional composition comprising a prebiotic mixture comprising polydextrose and galactooligosaccharide, between about 0.1 g and about 5 g per 100 kcal extensively hydrolyzed pectin having a peak molecular weight of 3,300 or less, and at least one insoluble fiber.

2. A method for providing prebiotics to a formula-fed infant while reducing the incidence of diarrhea in the infant, the method comprising administering to the infant a nutritional composition comprising a prebiotic mixture comprising polydextrose and galactooligosaccharide, between about 0.1 g and about 5 g per 100 kcal extensively hydrolyzed pectin having a peak molecular weight of 3,300 or less, and at least one insoluble fiber.

3. The method according to claim 2 wherein the amount of the prebiotic mixture is between about 1.0 g/L and 10.0 g/L of the nutritional composition.

4. The method according to claim 2 wherein the amount of the prebiotic mixture is between about 2.0 g/L and 8.0 g/L of the nutritional composition.

5. The method according to claim 2 wherein the amount of hydrolyzed pectin is between about 0.25 g and about 1 g per 100 kcal of the nutritional composition.

6. The method according to claim 1 wherein the amount of the prebiotic mixture is between about 1.0 and about 10.0 grams per liter of the nutritional composition.

7. The method according to claim 1 wherein the amount of the prebiotic mixture is between about 2.0 and about 8.0 grams per liter of the nutritional composition.

8. The method according to claim 1 wherein the amount of hydrolyzed pectin is between about 0.25 g and about 1 g per 100 kcal of the nutritional composition.

9. The method according to claim 1, wherein the nutritional composition additionally comprises at least one long chain polyunsaturated fatty acid.

10. The method according to claim 9, wherein the long chain polyunsaturated fatty acid comprises docosahexaenoic acid (DHA) or arachidonic acid (ARA).

11. The method according to claim 1, wherein the nutritional composition additionally comprises at least one probiotic.

12. The method according to claim 11, wherein the probiotic is selected from the group consisting of *Bifidobacteria* spp. and *Lactobacillus* spp.

13. The method according to claim 1, wherein the at least one insoluble fiber is selected from the group consisting of oat hull fiber, soy fiber, pea fiber, beet fiber, cellulose and corn fiber, and a mixture thereof.

14. The method according to claim 2, wherein the at least one insoluble fiber is selected from the group consisting of oat hull fiber, soy fiber, pea fiber, beet fiber, cellulose and corn fiber, and a mixture thereof.

15. The method according to claim 10, wherein the nutritional composition comprises DHA and ARA, further wherein the weight ratio of ARA to DHA is from about 1:3 to 9:1.

* * * * *